United States Patent [19]
Lohr

[11] Patent Number: 4,947,695
[45] Date of Patent: Aug. 14, 1990

[54] APPARATUS FOR CONTROLLING A STAR WHEEL FOR POSITIONING SPECIMEN CONTAINERS

[76] Inventor: Willy Lohr, Ginsterweg 75, D-7547 Wildbad, Fed. Rep. of Germany

[21] Appl. No.: 452,624

[22] Filed: Dec. 19, 1989

[30] Foreign Application Priority Data

Dec. 24, 1988 [DE] Fed. Rep. of Germany ... 8816086[U]

[51] Int. Cl.⁵ .............................................. G01N 1/00
[52] U.S. Cl. ................................. 73/ 863.01; 318/480
[58] Field of Search ........................ 73/863.01, 864.23; 250/231 SE; 198/339.1, 341; 422/63, 64; 318/480

[56] References Cited

U.S. PATENT DOCUMENTS

| 2,985,283 | 5/1961 | Carter | 198/341 |
| 3,381,570 | 5/1968 | Anway et al. | 88/14 |
| 4,204,115 | 5/1980 | Boldridge | 250/277 |
| 4,410,269 | 10/1983 | Jeffrey | 356/138 |
| 4,634,575 | 1/1987 | Kawakami et al. | 422/64 |
| 4,638,155 | 1/1987 | Dorr | 250/231 SE |
| 4,693,867 | 9/1987 | Commarmot et al. | 422/64 |
| 4,847,544 | 7/1989 | Goldberg | 318/696 |

FOREIGN PATENT DOCUMENTS

| 3013868 | 10/1980 | Fed. Rep. of Germany . | |
| 3447728 | 6/1986 | Fed. Rep. of Germany . | |
| 0211823 | 11/1984 | Japan | 250/231 SE |
| 1575636 | 9/1980 | United Kingdom . | |

OTHER PUBLICATIONS

Schlenk, Dipl.-Ing. Klaus W., "Sensoren und Aktoren auf magnetischer Basis", *Elektronic* 24/3.12.1982, pp. 96–98.

Dollwetzel, Von Dipl.-Ing. R. H., "Eigenschaften und Anwendungen von Reflexlichtschranken", Feinwerktec-nik & Messtechnik [*Precision Instruments and Measuring Instruments*] 93, 1985, 7, pp. 369–371.

*Primary Examiner*—Robert Raevis
*Attorney, Agent, or Firm*—Spensley Horn Jubas & Lubitz

[57] ABSTRACT

An apparatus for controlling a star wheel for precise positioning of specimen containers in circumferentially successive segments of the star wheel. The apparatus includes at least two sensor arrays, each including a transmitter and receiver, which are angularly offset from one another in the plane of rotation of the star wheel and face end surfaces of segmental vanes of the star wheel. Each time the star wheel reaches a defined angular position, one of the sensor arrays responds, and the output signal of this sensor array, via a control circuit, triggers a drive motor for the star wheel such that its rotational speed is reduced, and the output signal of the other sensor array, when the same segment moves past it, stops the motor. With this kind of two-stage triggering of the motor, the inertia of such a star wheel in its rotation is taken into account, so that the star wheel is controllable exactly in such a way that the specimen containers come to a stop successively and with high precision at the desired stopping position, where one or more processing steps, such as a measurement of luminescence, can be performed. By scanning the star wheel with the two sensor arrays directly at its circumference, additional components such as control disks, which are an additional source of error and reduce the precision, can be dispensed with.

8 Claims, 2 Drawing Sheets

APPARATUS FOR CONTROLLING A STAR WHEEL FOR POSITIONING SPECIMEN CONTAINERS

BACKGROUND OF THE INVENTION

The invention relates to an apparatus for controlling a star wheel for the exact positioning of specimen containers which are disposed in N segments of the star wheel such that the specimen containers succeed one another around the circumference of the star wheel and are moved by the star wheel incrementally in succession to a desired stopping position, the apparatus further having a drive motor that acts upon the star wheel and is controlled to rotate in increments.

Such star wheels are used in measurement technology, for example, to carry a number of specimen containers, e.g., test tubes, chained together, for the performance of various processing steps at respective processing locations, and to enable large-scale automation of these processing steps, as disclosed in Federal Republic of Germany DE-OS No. 30 13 868. A prerequisite for such an automatic succession of processing steps, for example in performing a luminescence measurement, adding liquids by pipette, and so forth, is that the drive of the star wheel be controllable so exactly that precise positioning of each specimen container is possible relative to the apparatus by which such a method step is performed. Accordingly, the star wheel must be stopped at exactly defined angular intervals and at an exactly defined position of the specimen containers conveyed, for the duration of the particular processing or measurement operation. DE-OS No. 30 13 868 provides no information as to how this could be satisfactorily accomplished.

A comparable problem in the precise processing of work pieces can be found in Federal Republic of Germany DE-OS No. 34 47 728, and the apparatus shown there is for this purpose embodied such that on the shaft of the work piece to be positioned, a control disk rotates in synchronism with the work piece, and this control disk is scanned with the aid of a bifurcated light gate.

The disadvantages of this previously known apparatus are substantially that the friction among the various components and the resultant slip, or inexact assembly, can make it impossible to assure an unequivocally defined association of the scanned marking in the control disk to the position of the workpiece, which must be equally precisely defined. It is therefore impossible to apply this principle to the exact positioning of specimen containers.

It is also generally known to use a reflex light gate, as disclosed in the publication entitled "Eigenschaften und Anwendungen von Reflexlichtschranken" [Properties and Applications of Reflex Light Gates] by Dipl.-Ing. R. H. Dollwetzel, Munich, which appeared in *Feinwerktechnik & Messtechnik* [*Precision Instruments and Measuring Instruments*] 93, 1985, 7, pp. 369–371, FIG. 5), for instance for detecting the teeth of a gear wheel.

A comparable application of a reflex light gate is also disclosed in U.S. Pat. No. 4,204,115 for measuring the circumferential speed of the disk of an electrical power meter.

All of these disclosures relate to the monitoring of a continuously moving object by means of a reflex light gate; in the type of apparatus with which this invention is concerned, however, operation is discontinuous and incremental, and for exact positioning of the specimen containers dynamic influences, in particular inertia effects of the rotating masses, must also be taken into account.

SUMMARY OF THE INVENTION

It is therefore an object of the invention to improve an apparatus of this generic type so that under such operating conditions it enables exact control of the star wheel in a way to assure a defined stopping position of the successive specimen containers for the performance of method steps such as measurements.

The above and other objects are achieved, according to the present invention, in apparatus including a star wheel having a cylindrical periphery provided with a plurality of recesses spaced apart around the periphery and a plurality of radially outwardly projecting vanes interposed between successive recesses for precisely positioning a respective specimen container in each recess, a shaft supporting the star wheel for rotation about a central axis, and an electrically controlled motor coupled to the shaft for rotating the star wheel in steps in a given direction of rotation for bringing each specimen container in turn to a defined position, by the improvement wherein said vane has a radially outwardly facing surface which is at least partially light reflective, and the apparatus further comprises at least two sensor arrays each comprising a light transmitter and a light receiver, the sensor arrays being angularly offset from one another by a defined angle about the central axis and each sensor array being disposed adjacent the path of movement of the vanes during rotation of the star wheel so that when a respective vane is opposite a respective sensor array, light emitted by the light transmitter will be reflected by the at least partly light reflective surface to the light receiver to cause the light receiver to produce an electrical signal, and a control circuit connected for controlling the rotation of the motor in response to the electrical signals produced by the light receivers of the sensor arrays, the sensor arrays being positioned and the control circuit being operative such that an electrical signal produced by the light receiver of a first one of the sensor arrays causes a reduction in the rate of rotation of the motor and an electrical signal produced by the light receiver of a second one of the sensor arrays causes the motor to stop at a defined angular position corresponding to the defined position of a respective specimen container.

Accordingly, the basic concept of the invention is substantially to control rotation of the star wheel by directly scanning the star wheel itself. As a result, additional components such as control disks, which also represent an additional possible source of error, can be eliminated. In addition, because of the stepwise reduction in the rotating frequency of the drive motor, a precise adherence to the desired stopping position of the star wheel is assured.

Further features of the invention are disclosed below.

An exemplary embodiment of the apparatus according to the invention is described in detail below, with reference to the drawings.

DESCRIPTION OF THE PREFERRED EMBODIMENTS

Figure 1:
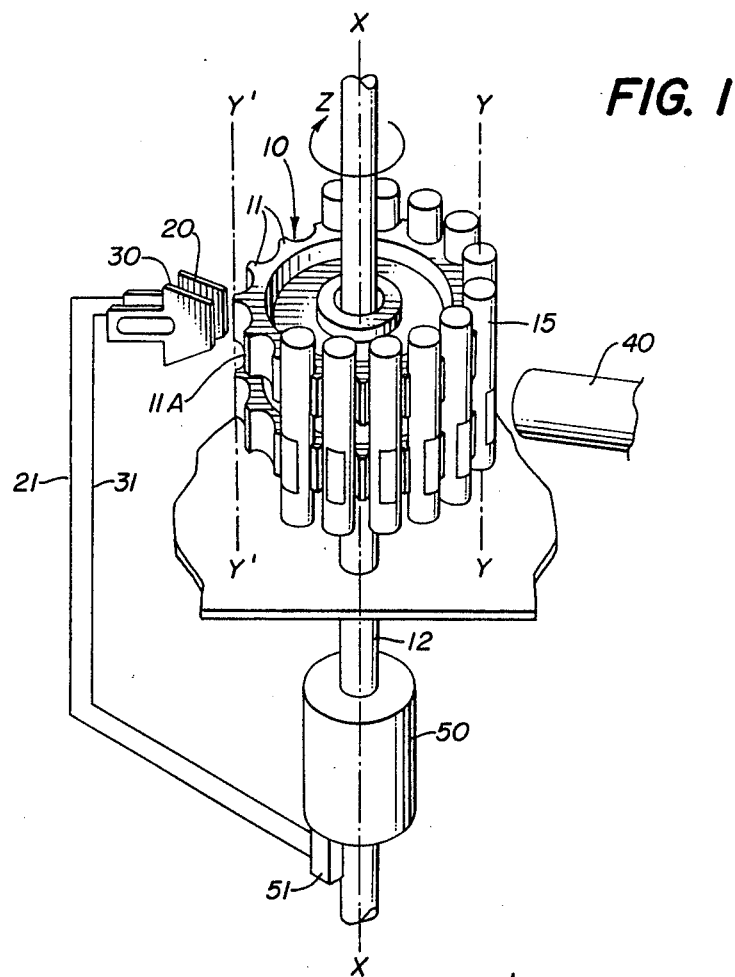
FIG. 1 is a basic perspective view of the entire apparatus constructed according to a preferred embodiment of the invention.
Figure 2:
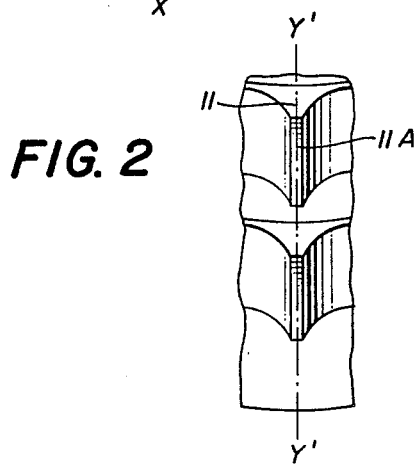
FIG. 2 is an elevational detail view illustrating the end face of a segmental vane of the apparatus of FIG. 1.
Figure 3:
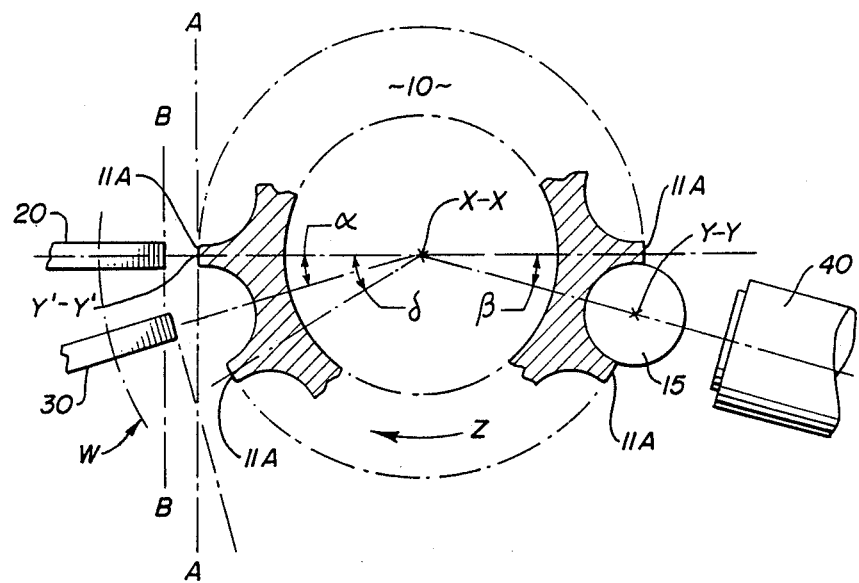
FIG. 3 is a schematic plan view, partly in cross section, of the star wheel and associated devices of the apparatus of FIG. 1.

The star wheel 10 shown particularly in FIGS. 1 and 3 serves the purpose of incremental advance of a chain of specimen containers 15 along a circular arc in the direction of the arrow Z (FIG. 1). To this end, star wheel 10 is fixed and supported on a shaft 12 which is engaged by a motor 50 that brings about the desired rotation. For grasping and transporting the chained together specimen containers 15, the star wheel has a plurality of segments, or recesses, which are separated from one another by segmental vanes 11 pointing outwardly, so that these segmental vanes 11 can engage in the interstices between adjacent specimen containers 15 in a gearwheel-like manner. Such star wheels are widely used in measuring technology, in particular for medical purposes, whenever measurements are to be performed successively on successive specimen containers 15.

In the exemplary embodiment shown here, a measuring instrument 40 is shown, which may for instance be a photomultiplier which is used to perform luminescence measurements on the contents of the specimen containers 15. Such measuring methods are known in detail and need not be described particularly here; the only decisive feature, with respect to the present invention, is that for satisfactory measurement, each specimen container 15 must assume a precisely defined position relative to measuring instrument 40, which position is indicated in the basic diagram of FIG. 3 by the angle $\beta$ between a spatially fixed reference plane containing the axis of rotation, X—X, of shaft 12 and a plane containing axis X—X and a vertical line Y—Y representing the precisely defined position relative to measuring instrument 40. The control of the star wheel 10 must accordingly assure that after each incremental rotation of wheel 10 by an angle $\delta$ (the angular spacing between successive segmental vanes 11), the vertical axis of the next specimen container 15 in succession is again precisely coincident with the axis Y—Y, or that the angle $\beta$ is precisely set once again. Only then are reproducible and preferably mutually comparable measurements of the contents of the specimen containers 15 assured.

In order to accomplish this, the apparatus shown utilizes the principle of the reflex, or reflecting, light gate constituted by a sensor array 20 in combination with a specially formed three-dimensional embodiment of the end face edges of the segmental vanes 11.

Figure 4:
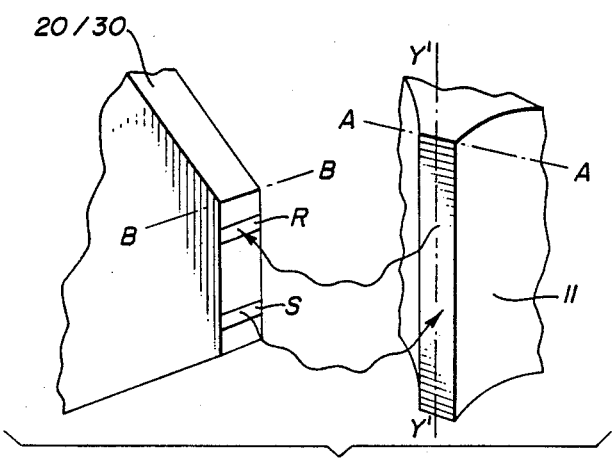
FIG. 4 is a perspective detail view of a portion of the embodiment of FIG. 1, with parts pivoted relative to their normal position.

These outer end face edges 11A are provided with a reflecting face that in the exemplary embodiment shown is approximately 0.5 mm wide and, for instance, is suitably milled. This face serves to reflect the light signal of sensor array 20, which, as shown in FIG. 4, is composed substantially of a transmitter S and a receiver R. The remainder of the surface of star wheel 10, and particularly the segments between vanes 11, is made nonreflecting, for instance being provided with an anodized black coating or finish.

Accordingly, the reflection condition is met if an end edge face 11A of the segmental vane 11, which end face edge has the form described above and lies in a plane A—A, is located directly opposite the sensor array 20, or in other words when plane A—A is located parallel to a plane B—B in which transmitter S and receiver R are located. If this condition is met, the light transmitted by the transmitter S is reflected at maximum intensity into the receiver R; that is, the vertical center line Y'—Y' of the opposed end edge face 11A has a defined angular position relative to angle $\beta$, so that the axis of a specimen container 15 can be aligned with axis Y—Y by corresponding positioning of sensor array 20 along a vertical arc plane W, shown in FIG. 3. The reflection condition is then optimally met precisely if the center axis of the applicable specimen container 15 coincides with axis Y—Y.

In the exemplary embodiment shown, the planes A—A and B—B are at a tangent to the star wheel 10. This is not absolutely necessary as long as the planes A—A and B—B extend parallel to one another.

Returning to FIG. 1, a first control line 21 connected to sensor array 20 conducts, in response to occurrence of the reflection condition, a reflection condition signal to a control circuit 51 operatively associated with motor 50 to stop motor 50 in response to such signal. Depending on the structural characteristics of the star wheel and the operating characteristics of the motor 50, it may be necessary here to adjust the position of sensor array 20, along plane W, in such a way that its reflection condition signal is emitted a short time prior to the attainment of the desired angular position of specimen container 15, in order to take inertia of the apparatus into account.

In order to define this effective inertia more precisely, in the illustrated exemplary embodiment a second sensor array 30 is provided, the operation of which is identical to that of the first sensor array 20; that is, once again, given the existence of the reflection conditions, a suitable signal is emitted via a second control line 31 to control circuit 51 of motor 50. The differences are as follows:

The second sensor array 30 is angularly offset from the first sensor array 20 by an angle $\alpha$ about axis X—X counter to the direction of rotation of star wheel 10; this means that each segmental vane 11, with its front end edge face 11A, first passes the second sensor array 30 before it reaches the first sensor array 20. If the reflection condition is sensed by the sensor array 30 (as described above with reference to sensor array 20), then the signal transmitted by sensor array 30 to control circuit 51 causes a reduction of the rotary speed of the motor 50, so that the remaining rotational angle $\alpha$ from the applicable end edge face 11A until that face comes into position opposite first sensor array 20 is traversed with decreasing circumferential speed. By this compulsory guidance of the motor 50 with the preceding second sensor array 30, the above-indicated theoretically possible inaccuracies from the effects of inertia of the entire apparatus can be reduced to a minimum; this means that it is assured with maximum precision that once the reflection condition pertains obtains for first sensor array 20, star wheel 10 will in fact stop at a position such that the exact positioning that, in the final analysis, is sought for the respective specimen container 15 (axis Y—Y or angle $\beta$) relative to the measuring instrument 40 is assured.

Depending on the structural embodiment of the entire apparatus, it may also be useful to provide a plurality of such additional sensor arrays preceding the primary array, in order to assure a definite specification of the rotary speed of the motor.

This application relates to subject matter disclosed in Federal Republic of Germany Application P G No. 88 16 086.6, filed on Dec. 24, 1988, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In apparatus including a star wheel having a cylindrical periphery provided with a plurality of recesses spaced apart around the periphery and a plurality of radially outwardly projecting vanes interposed between successive recesses for precisely positioning a respective specimen container in each recess, a shaft supporting the star wheel for rotation about a central axis, and an electrically controlled motor coupled to the shaft for rotating the star wheel in steps in a given direction of rotation for bringing each specimen container in turn to a defined position, the improvement wherein each said vane has a radially outwardly facing surface which is at least partially light reflective, and said apparatus further comprises at least two sensor arrays each comprising a light transmitter and a light receiver, said sensor arrays being angularly offset from one another by a defined angle about the central axis and each said sensor array being disposed adjacent the path of movement of said vanes during rotation of said star wheel so that when a respective vane is opposite a respective sensor array, light emitted by said light transmitter will be reflected by said at least partly light reflective surface to said light receiver to cause said light receiver to produce an electrical signal, and a control circuit connected for controlling the rotation of said motor in response to the electrical signals produced by said light receivers of said sensor arrays, said sensor arrays being positioned and said control circuit being operative such that an electrical signal produced by said light receiver of a first one of said sensor arrays causes a reduction in the rate of rotation of said motor and an electrical signal produced by said light receiver of a second one of said sensor arrays causes said motor to stop at a defined angular position corresponding to the defined position of a respective specimen container.

2. Apparatus as defined in claim 1 wherein said light transmitter and light receiver of each said sensor array are spaced apart in a direction parallel to said central axis.

3. Apparatus as defined in claim 2 wherein said outwardly facing surface of each said vane is oriented to be tangent to a circle centered on said central axis, and said light transmitter and light receiver of each said sensor array are oriented so that when said outwardly facing surface of a said vane is opposite a respective sensor array, said light transmitter and light receiver of that sensor array are parallel to said outwardly facing surface.

4. Apparatus as defined in claim 3 wherein the defined angle by which said sensor arrays are offset from one another is smaller than the angular spacing, about said central axis, between successive vanes.

5. Apparatus as defined in claim 1 wherein, at any given time, specimen containers are disposed in recesses only around a portion of the periphery of said star wheel and said sensor arrays are disposed in a circumferential region of said star wheel where specimen containers are not present.

6. Apparatus as defined in claim 1 wherein each said sensor array is an optical reflex light gate.

7. Apparatus as defined in claim 1 wherein said sensor arrays are displaceable along a cylindrical plane centered on said central axis.

8. Apparatus as defined in claim 1 wherein at least a light reflective portion of said radially outwardly facing surface of each said vane is planar.

* * * * *